(12) United States Patent
Wray et al.

(10) Patent No.: US 6,332,878 B1
(45) Date of Patent: Dec. 25, 2001

(54) DEVICES AND METHODS FOR CAPTURING AND CONTAINING MENSTRUAL FLOW

(75) Inventors: Daniel X. Wray, Vista; Lisa A. O'Carroll, Oceanside; Robert S. Billups, Vista; Thomas D. Walter, San Marcos; Harold L. Knudsen, Escondido; Lara A. Kasum, Vista; Robert L. DeArmond, Oceanside; Cher Haavind, Encinitas, all of CA (US)

(73) Assignee: Moonstruck, LLC, Vista, CA (US)

( * ) Notice: Subject to any disclaimer, the term of this patent is extended or adjusted under 35 U.S.C. 154(b) by 0 days.

(21) Appl. No.: 09/388,893

(22) Filed: Sep. 2, 1999

(51) Int. Cl.$^7$ .................................................. A61F 5/44
(52) U.S. Cl. ............................ 604/328; 600/582; 128/830
(58) Field of Search .................... 604/385.17, 385.18, 604/327–331; 128/830; 600/574, 580, 582

(56) References Cited

U.S. PATENT DOCUMENTS

| | | | |
|---|---|---|---|
| 2,089,113 | 8/1937 | Chalmers | 128/285 |
| 2,534,900 | 12/1950 | Chalmers | 128/285 |
| 2,616,426 | 11/1952 | Gordon | 128/285 |
| 3,128,767 | 4/1964 | Nolan | 128/285 |
| 3,404,682 | 10/1968 | Waldron | 128/285 |
| 3,626,942 | 12/1971 | Waldron | 128/285 |
| 3,794,029 | 2/1974 | Dulle | 128/285 |
| 3,815,601 | 6/1974 | Schaefer | 128/285 |
| 3,841,333 | 10/1974 | Zalucki | 128/285 |
| 3,845,766 | 11/1974 | Zoller | 128/285 |
| 4,271,835 | 6/1981 | Conn et al. | 128/270 |
| 4,286,596 | 9/1981 | Rubinstein | 128/270 |
| 4,318,404 | 3/1982 | Cunningham | 128/263 |
| 4,320,751 | 3/1982 | Loeb | 128/127 |
| 4,359,357 | 11/1982 | Friese | 156/201 |
| 4,374,522 | 2/1983 | Olevsky | 128/285 |
| 4,381,771 | 5/1983 | Gabbay | 128/129 |
| 4,401,534 | 8/1983 | Goepp et al. | 264/138 |
| 4,424,054 | 1/1984 | Conn et al. | 604/11 |
| 4,450,836 | 5/1984 | Goepp et al. | 128/127 |
| 4,517,970 | 5/1985 | Goepp et al. | 128/131 |
| 4,648,867 | 3/1987 | Conner et al. | 604/14 |
| 4,681,579 | 7/1987 | Toussant et al. | 604/385 R |
| 4,799,929 | 1/1989 | Knowles | 604/331 |
| 4,846,802 | 7/1989 | Sanders, III | 604/15 |
| 4,848,363 | 7/1989 | Cattanach | 128/834 |
| 4,857,044 | 8/1989 | Lennon | 604/14 |
| 4,955,875 | 9/1990 | Knowles | 604/331 |
| 4,961,436 | 10/1990 | Koch | 128/837 |
| 5,158,535 | 10/1992 | Paul et al. | 604/15 |
| 5,295,984 | 3/1994 | Contente et al. | 604/317 |
| 5,348,534 | 9/1994 | Tomaszewski et al. | 604/14 |
| 5,437,628 | 8/1995 | Fox et al. | 604/14 |
| 5,471,820 | 12/1995 | Oppe et al. | 53/449 |
| 5,531,674 | 7/1996 | Frayman | 604/11 |
| 5,533,990 | 7/1996 | Yeo | 604/363 |
| 5,554,108 | 9/1996 | Browning et al. | 604/15 |
| 5,554,109 | 9/1996 | Frayman | 604/15 |
| 5,718,699 | 2/1998 | Brisebois | 604/385.1 |
| 5,827,248 | 10/1998 | Crawford | 604/328 |
| 5,928,184 | * 7/1999 | Etheredge et al. | 604/15 |
| 5,941,860 | * 8/1999 | Wheeler | 604/327 |
| 6,168,609 | * 1/2001 | Kamen et al. | 606/193 |

* cited by examiner

Primary Examiner—Dennis Ruhl
(74) Attorney, Agent, or Firm—The Brotman Group; Harris F. Brotman

(57) ABSTRACT

A device for collecting menstrual flow has a cup shaped to fit over the cervix and has an attached pouch defining a reservoir that contains an absorbent material. A port having a fabric cover permits menstrual flow from the uterus to pass into the reservoir. The device, which is flexible and resilient, is folded in one end of an applicator used to insert the device into the vagina. The device is shaped to automatically fit into and remain in position over the cervix after the device is ejected from the applicator.

14 Claims, 9 Drawing Sheets

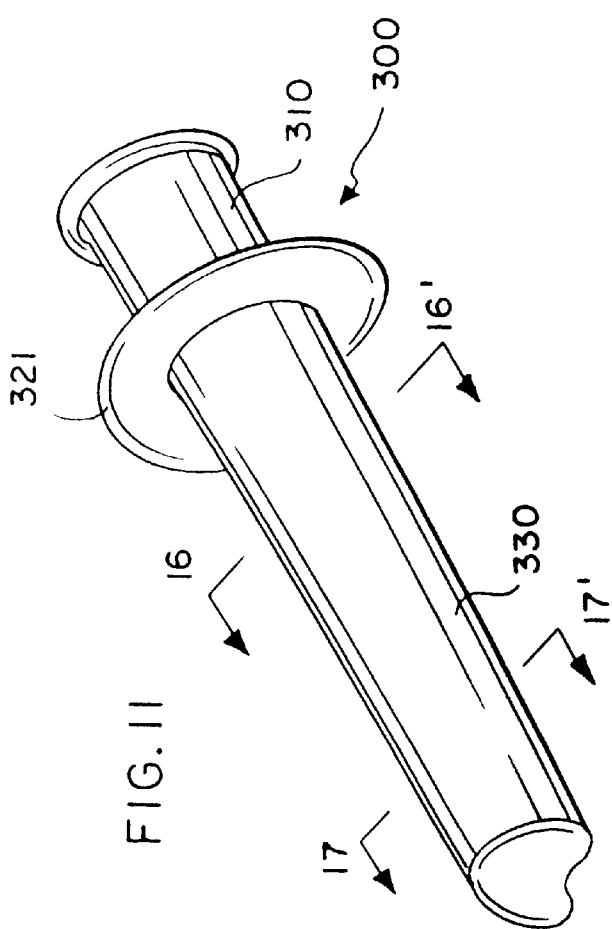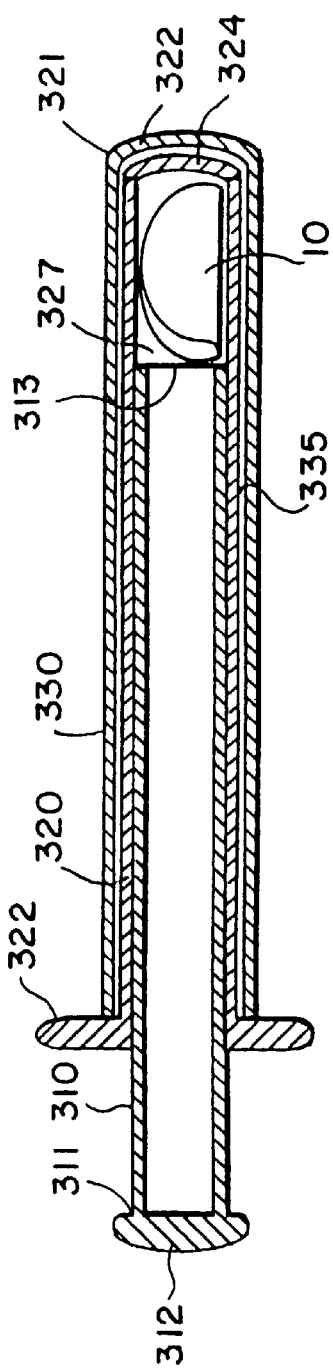

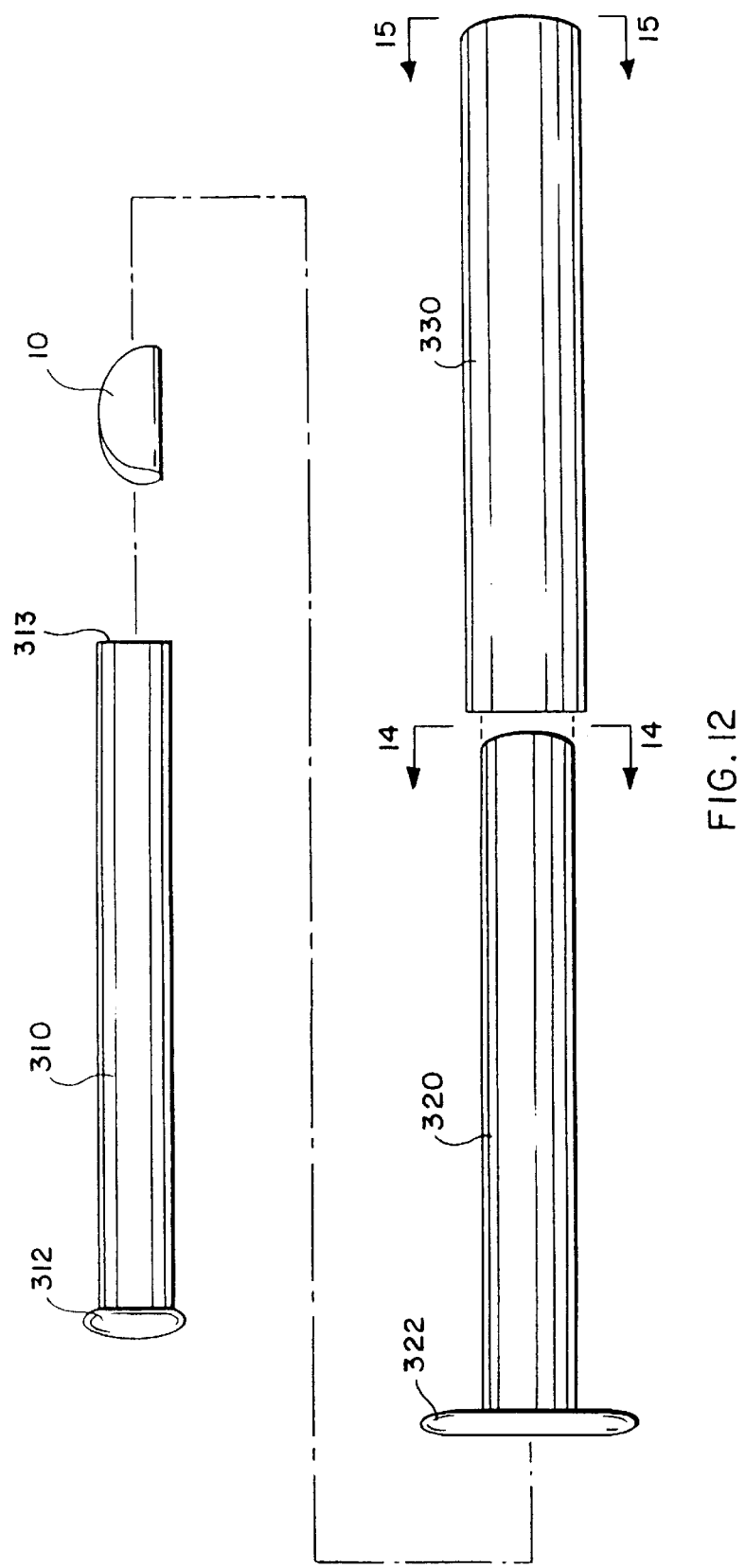

DEVICES AND METHODS FOR CAPTURING AND CONTAINING MENSTRUAL FLOW

BACKGROUND OF THE INVENTION

The invention relates generally to devices and methods for the collection of menstrual flow and other discharge from female humans, particularly during a menstrual period.

Menstrual flow from the uterus of female humans has traditionally been collected through the use of an absorbent material. The absorbent material has been formed into a tampon or sponge that is inserted into the vagina to receive and absorb the menstrual flow. See, e.g., U.S. Pat. No. 4,374,522 to Olevsky for a "Tampon with Central Reservoir." Tampons or sponges do not entirely eliminate leaks and must be replaced periodically when the absorptive capacity of the tampon or sponge is reached.

Furthermore, extended wear of high absorbency tampons may lead to an increased risk of toxic shock syndrome (TSS). TSS is believed to be caused by the ingress of bacteria cultured in the absorbent material into the body through lesions or lacerations of the vaginal lining. High absorbency tampons may cause such lesions or lacerations by drying the vaginal wall. In addition, tampons or sponges expose the vagina to bleaches and other chemicals contained in their absorbent material.

Another disadvantage of tampons and sponges is that they must be removed in order to permit sexual intercourse; intercourse, however, will be inevitably messy because the menstrual flow will no longer be checked.

In the alternative, the absorbent material may be formed into a pad that is positioned immediately below the introitus or opening of the vagina to receive and absorb the menstrual flow. See, e.g., U.S. Pat. No. 5,718,699 to Brisebois for "Disposable Absorbent Product with Secondary Liquid-Containment Structure." These devices are large and bulky and may allow leakage when disarranged by the wearer's movement or improperly worn.

Other devices have been devised over the years for the purpose of collecting or at least blocking menstrual flow. These include menstrual cups that abut the walls of the vagina and block the passage of fluids from the cervix to the exit of the vagina. See, e.g., U.S. Pat. No. 3,845,766 to Zoller for "Cup-Shaped Device for the Collection of Menstrual Fluids and Intended for Internal Use." Such devices are uncomfortable and can leak or overflow when removed. Also, these devices are reusable and must be washed after use.

Other internally placed devices have structures like the diaphragms used for contraception. Such devices are thus large and round in order to cover the cervix and a large part of the upper vaginal wall. See, e.g., U.S. Pat. No. 5,295,984 to Contente, et al. for "Vaginal Discharge Collection Device and Intravaginal Drug Delivery System" and U.S. Pat. No. 4,848,363 to Cattanach for "Valved Vaginal Collection Device." All such devices, as with tampons, will be messy upon extraction, will increase the risk of toxic shock syndrome, or will interfere with sexual intercourse.

A device for collecting and containing menstrual flow therefore is needed that will not have the disadvantages noted above.

SUMMARY OF THE INVENTION

The invention provides a device for capturing and containing menstrual flow, comprising a cup shaped to substantially cover the cervix and having an intravaginal reservoir for collecting menstrual flow. Preferably, the cup has a first side substantially shaped and sized for sealing contact with the cervix and a port adjacent the external os of the cervix in order to permit the egress of menstrual flow discharged by the external os of the cervix from the first side of the cup into a reservoir defined by the cup and a pouch attached to the cup. The pouch is shaped to comfortably fit into the upper end of the vaginal canal below the cervix. An absorbent material, which may be treated with an antibacterial solution, may be placed in the reservoir for absorbing the menstrual flow received in the reservoir.

The cup and the pouch preferably are made of a flexible, resilient, and biocompatible plastic. The absorbent material preferably is made of an absorbent material such as polymer fibers. The cup and the pouch preferably will be separately formed by injection-molding or other forming process and then fastened together.

Resilient rings molded into the cup and the pouch-shaped wall may be provided to maintain the position of the device against and over the cervix and to maintain the seal of the cup of the device around the os of the cervix. Preferably, the device will contain a "posterior fornix spacer" that engages the posterior fornix (at the rear of the cervix) in order to maintain the position of the device.

The port preferably will be provided with a permeable cover in order to prevent captured menstrual flow from contacting the cervix. The permeable cover, which preferably will be a small piece of fabric or other material, also prevents the absorbent material from contacting the vaginal walls and thus reduces the risk of toxic shock syndrome. In addition, the permeable cover stops leakage of captured menstrual flow and thus contributes to the reduction of mess after removal of the device. Disposal of the device after use therefore will be less troublesome.

The device preferably will be equipped with a string in order to facilitate removal from the vagina.

The device preferably will be inserted using an applicator. The applicator is a plastic cylinder having a piston mounted inside. The device preferably is folded into an open end of the cylinder above the piston. The open end of the cylinder is inserted through the introitus or opening of the vagina until it is near the top of the vagina and adjacent the cervix. The cylinder is then withdrawn while not moving the piston so that the device is ejected from the cylinder. The device then unfolds and glides into the end of the vagina and automatically locks onto the cervix. Preferably, the device is coated with lubricant either when it is stored in the applicator or while it is being released from the applicator. The lubricant coating on the device will assist it to slip into place against the cervix.

OBJECTS AND ADVANTAGES OF THE INVENTION

It is an object of this invention to provide a device and method for capturing and containing menstrual flow that will isolate the captured menstrual flow from the vaginal lining and the cervix.

Another object of this invention is to provide a device and method of capturing and containing menstrual flow that will substantially reduce the risk of toxic shock syndrome.

A further object of this invention is to provide a device and method for capturing and containing menstrual flow for an extended period of time.

Yet another object of this invention to provide a device and method for capturing and containing menstrual flow that will permit little or no leakage of menstrual flow past the device.

An additional object of this invention is to provide a device and method for capturing and containing menstrual flow that will encapsulate the captured menstrual flow upon removal from the vagina.

Still another object of this invention is to provide a device for capturing and containing menstrual flow that will permit sexual intercourse while the menstrual flow is being captured and contained.

Yet an additional object of this invention is to provide a device and method for capturing and containing menstrual flow that is comfortable and convenient to use.

DESCRIPTION OF THE DRAWINGS

Other objects, features, and advantages of the present invention will become more fully apparent from the following detailed description of preferred embodiments, the appended claims, and the accompanying drawings in which:

FIG. 11 is a perspective view of a preferred embodiment of an applicator for insertion of the devices shown in FIGS. 1–9 into the vagina of a female human being;

FIG. 12 is an exploded view showing how the components of the applicator shown in FIG. 11 are assembled;

FIG. 13 is a cross-sectional side view of the applicator shown in FIG. 11 with one of the devices of FIGS. 1–9 folded into one end of the applicator;

Figure 1:
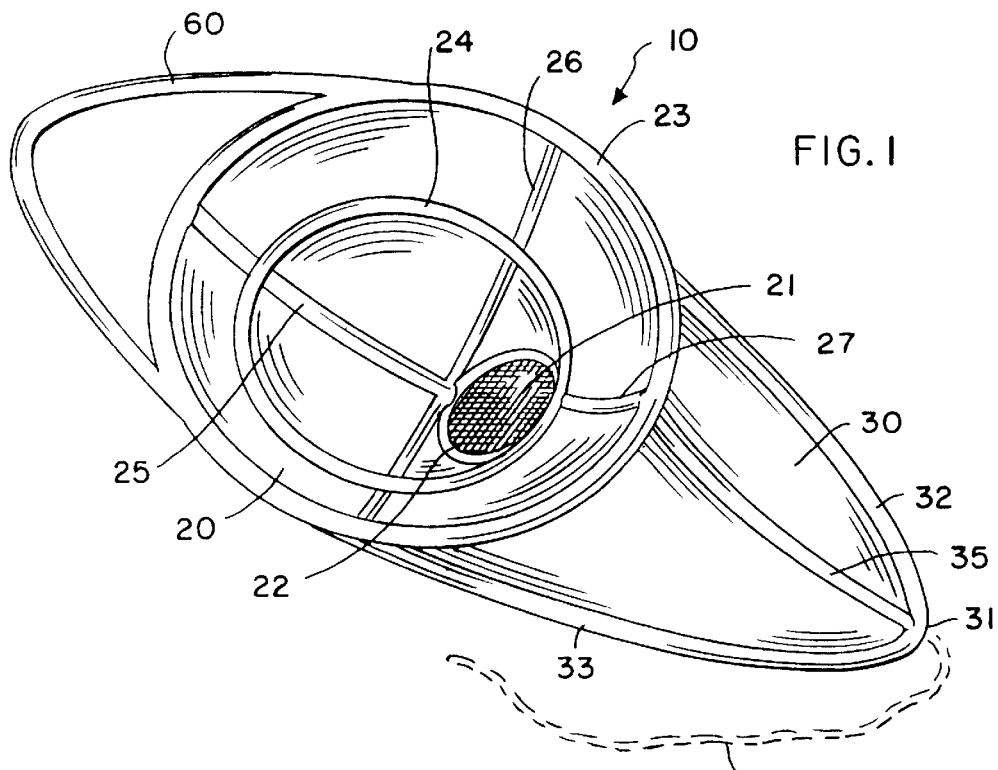
FIG. 1 is a perspective view of a preferred embodiment of a device for capturing and containing menstrual flow according to the invention.
Figure 2:
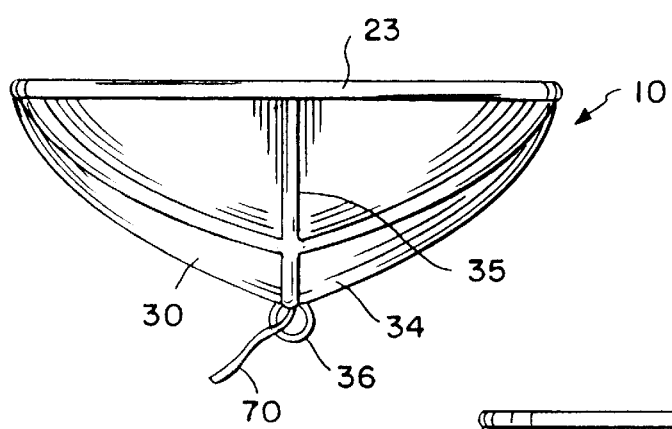
FIG. 2 is a plan view of the back or distal side of the device shown in FIG. 1.
Figure 3:
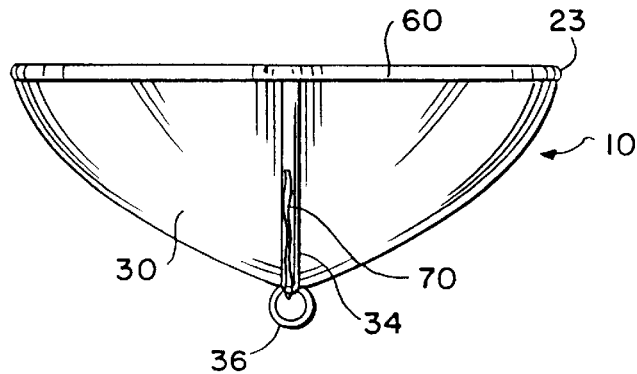
FIG. 3 is a plan view of the front or proximal side of the device shown in FIG. 1.
Figure 4:
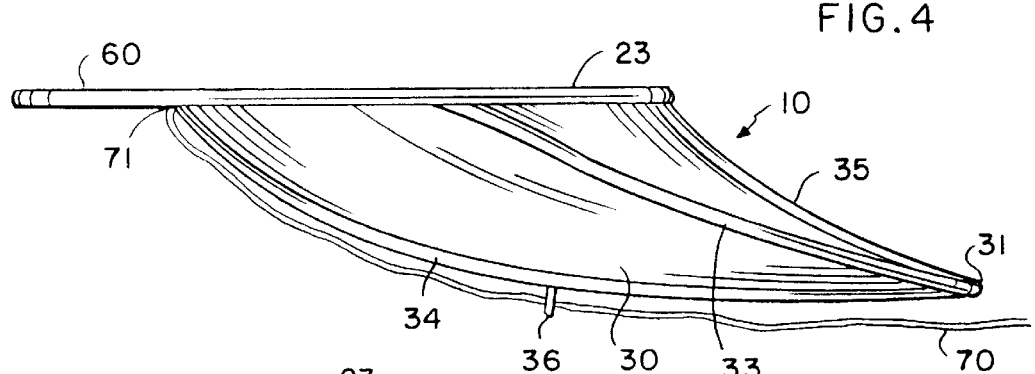
FIG. 4 is a plan view of one lateral side of the device shown in FIG. 1.
Figure 5:
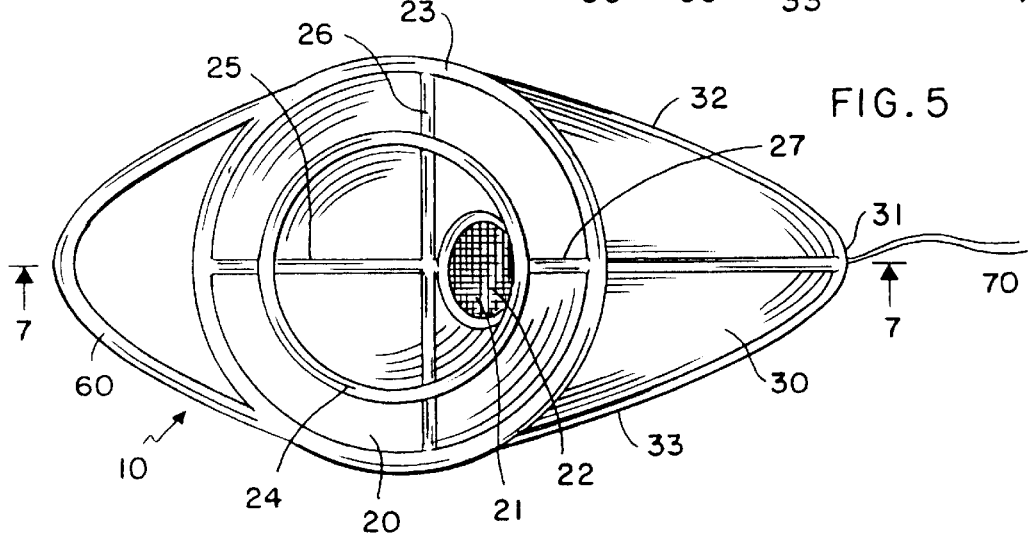
FIG. 5 is an elevation view of the device shown in FIG. 1.
Figure 6:
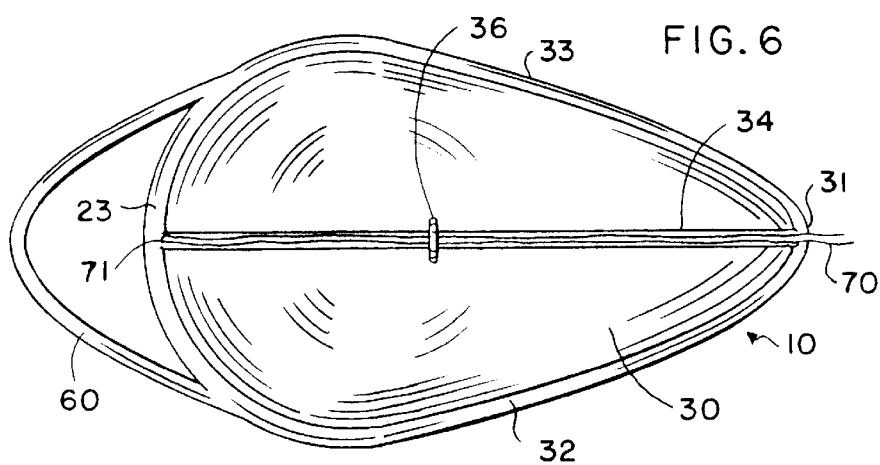
FIG. 6 is a bottom view of the device shown in FIG. 1.
Figure 7:
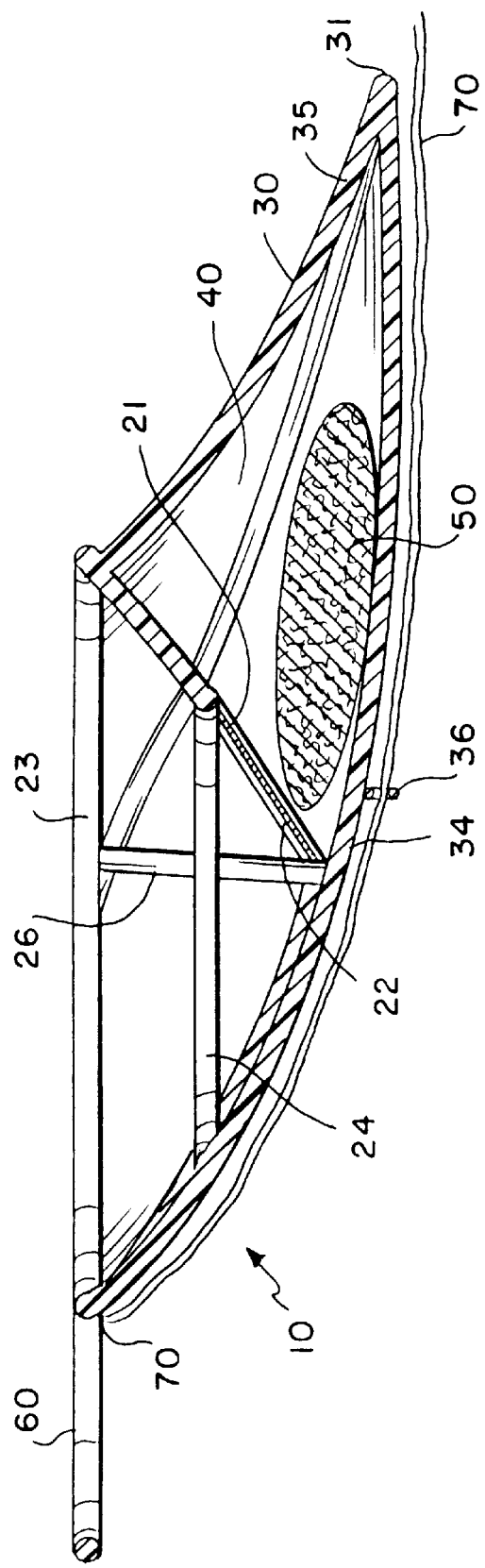
FIG. 7 is a cross-sectional view of the device shown in FIG. 1.

REFERENCE NUMERALS IN THE DRAWINGS 10 device for capturing and containing menstrual flow (first embodiment)
20 cup
21 port
22 port cover
23 outer rib
24 inner rib
25 radial rib
26 radial rib
27 radial rib
30 pouch
31 end
32 lateral rib
33 lateral rib
34 posterior rib
35 anterior rib
36 ring
40 reservoir
50 absorbent material
60 posterior fornix spacer
70 retrieval string
71 attachment point
100 device for capturing and containing menstrual flow (second embodiment)
110 cup
120 pouch
121 posterior rib
122 anterior rib
123 spiral rib
130 reservoir
140 absorbent bolus
200 device for capturing and containing menstrual flow (third embodiment)
210 cup
220 pouch
221 posterior rib
222 anterior rib
223 lateral rib
224 lateral rib
225 scale
226 end of pouch
300 applicator
310 piston
311 external end
312 cap
313 internal end
320 inner sleeve
321 distal end
322 flange
323 proximal end
324 cap
325 flaps
326 channel
327 chamber
328 groove
330 outer sleeve
331 first end
332 cap
333 channel
334 second end
335 space
340 direction of pressing flange
A anterior fornix
C cervix
O os
P posterior fornix
U uterus
V vagina

DETAILED DESCRIPTION OF THE PREFERRED EMBODIMENTS

Figure 10:
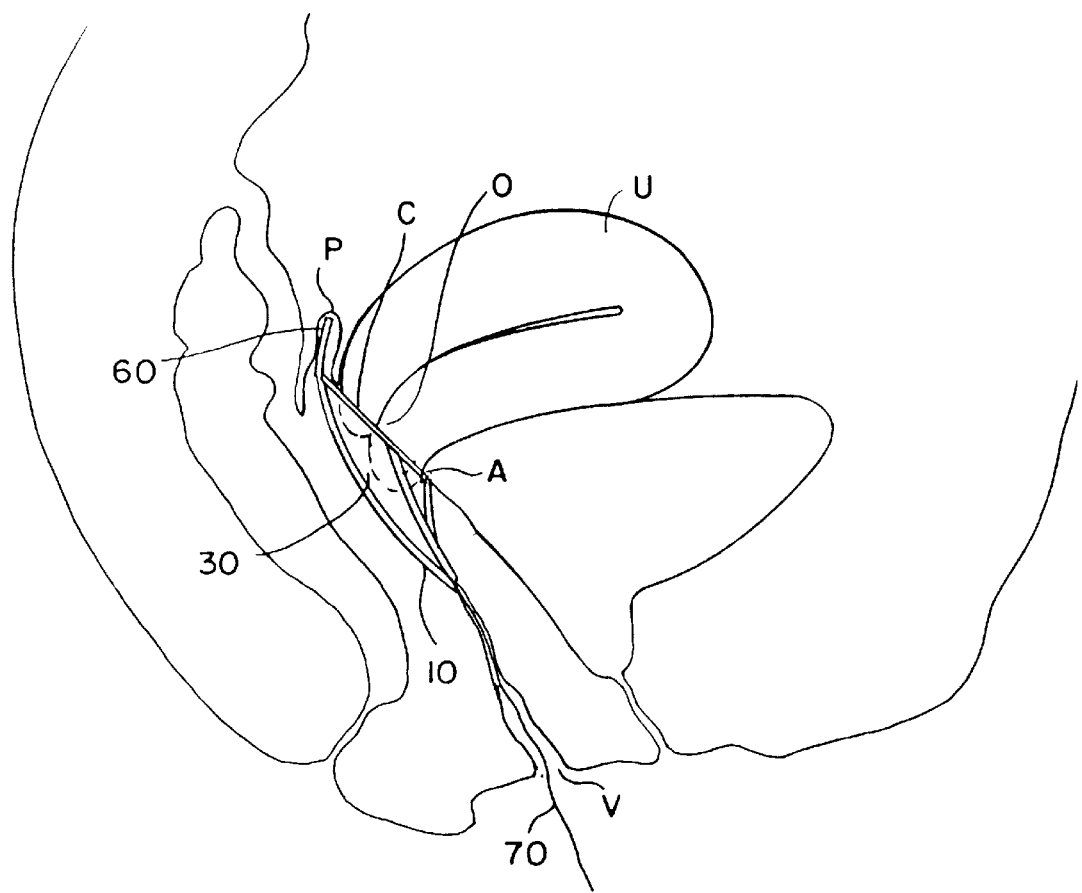
FIG. 10 is a side view showing the device of FIGS. 1–7 in place against the cervix of a female human being.
Figure 14:
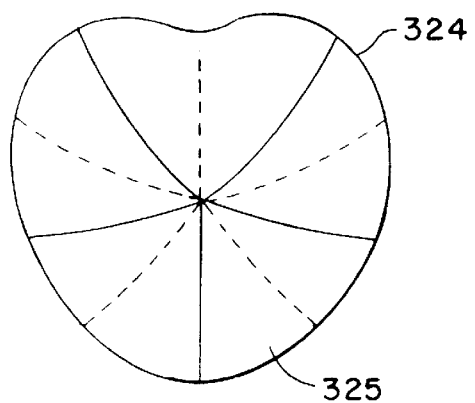
FIG. 14 is an end view of the inner sleeve of the applicator shown in FIG. 12.
Figure 15:
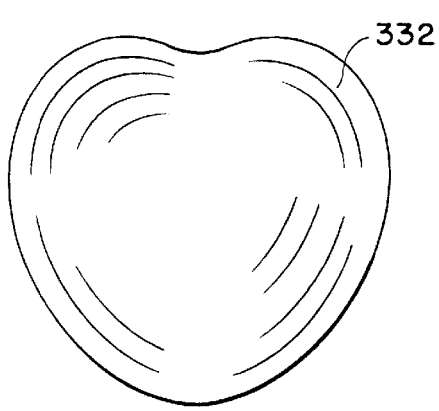
FIG. 15 is an end view of the outer sleeve of the applicator shown in FIG. 12.

A preferred embodiment of a device for capturing or collecting menstrual flow is shown in FIGS. 1–7. The device 10 has a cup 20 shaped and sized to fit over the cervix of a female human being in sealing contact. A pouch 30 is attached to the cup 20. The cup 20 and the pouch 30 surround and define a reservoir 40 (shown in FIG. 7). A port 21 penetrates the cup 20 and permits the passage of liquid into the reservoir 40. Preferably, the port 21 should be positioned as shown in FIG. 10 so that it is adjacent the os O of the uterus U when the device 10 is in position at the upper end of the vagina V and covering the cervix C.

The cup 20 has a circumferential outer rib 23 and a circumferential inner rib 24 that help maintain the generally circular shape of the cup 20. Radial ribs 25–27 formed in the cup 20 help maintain its generally hemispheric shape.

The cup 20 preferably is made of a flexible and resilient material. The cup 20 should be flexible and resilient in order to be able to return to its generally circular shape from a folded configuration when released in the vagina and then assume the correct position against and sealing the cervix. Acceptable materials include SANTOPRENE 281-35 and 281-45, available from Advanced Elastomer Systems of Akron, Ohio; ENGAGE POE8401 from Dupont Dow of Wilmington, Del.; and KRATON G2705 from Shell Chemical, distributed by GLS Corporation of Arlington Heights, Ill. SANTOPRENE 281-45 currently is preferred for the material of the cup 20.

The port 21 has a port cover 22 made of a material permeable to the ingress of menstrual flow. The currently preferred material is a layer or AIRLAID material available from Air Form Composites of Charleston, S.C. The port cover 22 permits the ingress of liquid into the reservoir 40 by a wicking action and will resist the exit of the liquid contained in the reservoir 40.

The port 21 could also be equipped with a one-way valve in place of the material of the port cover 22. Examples of one-way valve that might be so employed are disclosed in U.S. Pat. No. 4,381,771 to Gabbay. The disclosure of U.S. Pat. No. 4,381,771 is incorporated by reference into this specification as if fully set forth, and particularly with respect to its teaching of one-way valves.

The pouch 30 is shaped so that it comes to a closed end 31 and bends away, rather than projects, from the cup 20 so as to fit into the upper vagina V (see FIG. 10). The pouch 30 has two lateral ribs 32 and 33 that are connected to opposed sides of the cup 20 and converge into each other adjacent the end 31. Posterior rib 34 and anterior rib 35 are connected to opposed sides of the cup 20 between the lateral ribs 32 and 33. The posterior rib 34 and anterior rib 35 connect to the juncture of the lateral ribs 32 and 33 adjacent the end 31. The purpose of the ribs 32–35 is to give additional resilience to the pouch 30 so that it will return generally to the shape shown in FIGS. 1–7 when it is released from a furled configuration in the vagina. This shape mimics that of the upper part of the vagina in the vicinity of the cervix. The pouch 30 will thus help to hold the device 10 in position against the cervix because the pouch 30 will press against the vaginal walls.

The pouch 30 preferably is made of a flexible and resilient material. The pouch 30 should be flexible and resilient in order to be able to return to its generally drooped cone shape from a folded configuration when released in the vagina and then to bias the cup 20 into the correct position against and sealing the cervix. Acceptable materials include SANTO-PRENE 281-35 and 281-45, available from Advanced Elastomer Systems of Akron, Ohio; ENGAGE POE8401 from Dupont Dow of Wilmington, Del.; and KRATON G2705 from Shell Chemical, distributed by GLS Corporation of Arlington Heights, Ill. SANTOPRENE 281-45 currently is preferred for the material of the pouch 30.

The reservoir 40 contains an absorbent egg-shaped bolus 50. The bolus 50 preferably is made of Airlaid Material, a thermal bonded airlaid structure containing SXM 77 absorbent polymer that is available from Air Form Composites of Charleston, S.C. The bolus 50 may be impregnated with an antibacterial solution so as to resist the development of bacterial cultures in the menstrual flow absorbed by the bolus 50.

The bolus 50 will absorb the menstrual flow entering the reservoir 40 via the port 21 and will expand to fill the reservoir 40. Menstrual flow that enters through the port 21 therefore will not return through the port 21 because it will have been absorbed. The bolus 50, however, cannot contact the cervix or the vaginal walls because it is fully encapsulated by the cup 20 and the pouch 30. This encapsulation will reduce the risk of causing lesions in the vaginal walls. Furthermore, the captured menstrual flow will be isolated from the cervix and the vaginal walls. Any bacterial growth in the captured menstrual flow, therefore, will be isolated from the cervix and the vaginal walls. This will reduce the risk of toxic shock syndrome associated with high absorbency tampons.

A posterior fornix spacer 60 is attached to the outer rib 23 of the cup 20. It is preferably made of the same flexible and resilient material as the cup 20. Its purpose is to engage or press against the posterior fornix and thereby position the cup 20 over and against the cervix.

A retrieval string 70 is attached to the cup 20 at the attachment point 71 on the posterior side of the outer rib 23. It is passed through a ring 36 on the posterior rib 34. The retrieval string 70 trails from the device 10 and down the vagina. The user grasps the downstream end of the retrieval string 70 and pulls it. The retrieval string 70, which is free to slide through the ring 36, will pull on the attachment point 71 on the posterior side of the outer rib 23. This pull will torque the cup 20 off the cervix and then pull the device 10 downstream through the vagina and out for disposal.

The retrieval string 70 preferably is made of T35 ADMIRAL WHTO combed supima cotton thread from Coats North America of Charlotte, N.C.

The device 10 is constructed by performing the following steps. The cup 20 and the pouch 30 are injection-molded separately. The posterior fornix spacer 60 is molded as part of the cup 20. The absorbent bolus 50 is placed between the cup 20 and the pouch 30. The cup 20 and the pouch 30 are then ultrasonically welded together. The retrieval string 70 is then attached to the cup 20 and slid through the ring 36.

Exemplary dimensions of an embodiment of the device 10 are:

Diameter of cup 20 (to inside of outer rib 23): 3.4 centimeters;

Overall height: 2.8 centimeters;

Overall length: 7.25 centimeters;

Volume of absorbent bolus prior to exposure to menstrual flow: 0.756 cubic centimeters.

It will be understood that variations in various dimensions of the device 10 will be not only possible but also desirable in order to accommodate women of different sizes and menstrual flow volumes. Devices for collecting and containing menstrual flow according to the invention can be made to have different capacities so that the devices can accommodate greater or lesser flows and can be worn for shorter or longer times.

Figure 8:
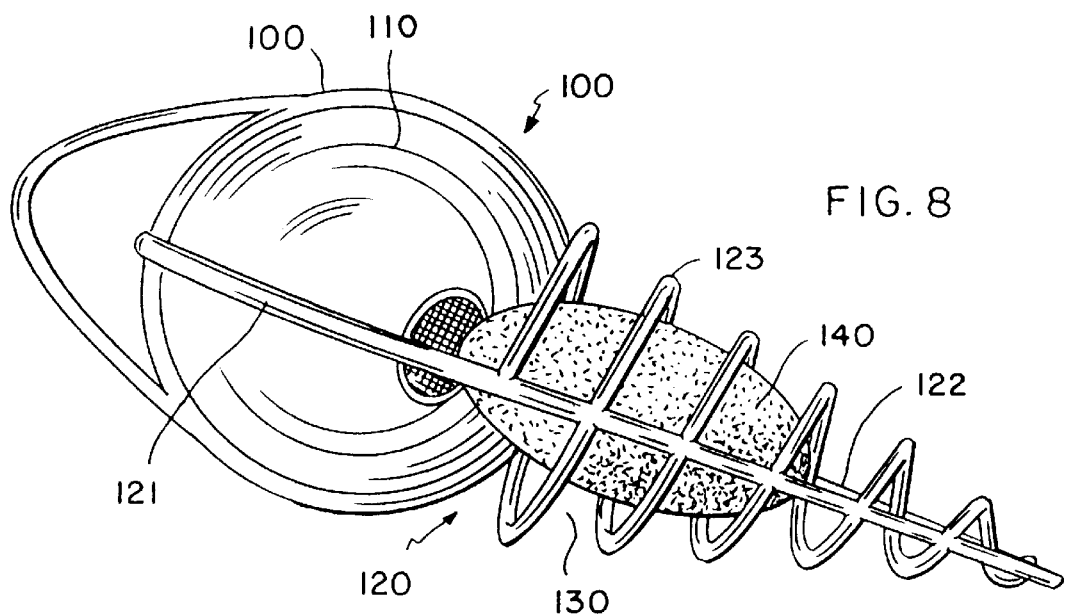
FIG. 8 is a bottom or posterior view of an alternative embodiment of a device for capturing and containing menstrual flow according to the invention.
Figure 9:
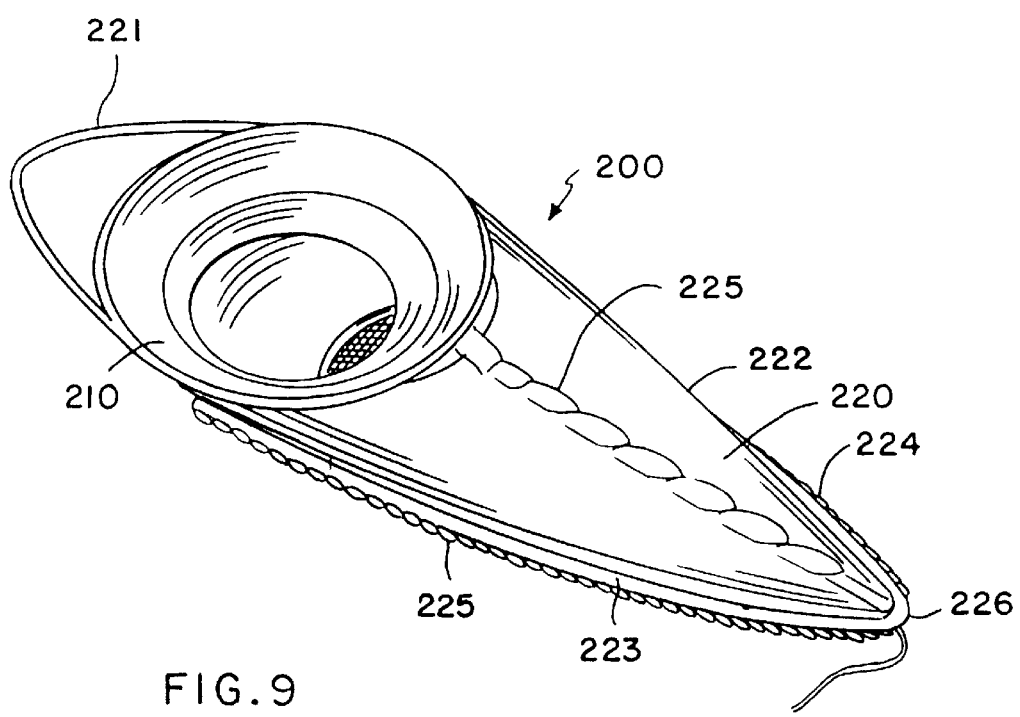
FIG. 9 is a perspective view of a second alternative embodiment of a device for capturing and containing menstrual flow according to the invention.

Alternate embodiments of a device according to the invention are shown in FIGS. 8 and 9.

FIG. 8 shows the posterior side of a device 100 having a cup 110 similar to that described in connection with the device 10 of FIGS. 1–7. The pouch 120, however, has a spiral rib 123 attached to a posterior rib 121 and an anterior rib 122. (The walls of the pouch 120 are not shown in FIG. 8 in order to show the rib structure with greater clarity. The retrieval string is also omitted for the same reason.) The ribs 121–123 surround the reservoir 130 that contains the absorbent bolus 140. The spiral shape of the rib 123 provides additional resilience and provides semi-automatic deployment of the device 100 to a sealing position against the cervix. Normal vaginal movement against the device 100 urges the device 100 into the end of the vagina and over the cervix.

FIG. 9 shows a device 200 having a cup 210 and a pouch 220 that could be constructed according to the design of either the device 10 or the device 100 described above. Scales 225 are molded onto the exteriors of the ribs 221–224 of the pouch 166 (the posterior rib 221 is not visible in FIG. 9). The scales 225 generally point to the end 226 of the pouch 220. The scales 225 engage the vaginal wall and cause the device 200 to resist movement downstream in the vagina. The scales 226 therefore assist the device 200 in finding its correct position at the end of the vagina and against the cervix.

A device 10 is shown in position in the vagina V of a female human being in FIG. 10. The alternate embodiments 100 and 200 will be similarly positioned at the end of the vagina and against the cervix C, between the anterior fornix A and the posterior fornix P. The posterior fornix spacer 60 enters the posterior fornix P and tensions the cup 20 against the cervix C so that a seal is established between the cup 20 and the cervix C so that all menstrual flow escaping from the os O will be captured and retained by the device 10.

The device 10 (and the alternate embodiments) is small, flexible, and resilient. It will be located in use at the end of the vagina. The device 10 will not interfere with sexual intercourse if it is made with pouch 30 that is small so that it does not extend any substantial distance down the vagina from the cervix.

The device 10 (or any of the alternative embodiments 100 or 200) preferably is inserted with the use of an applicator. A currently preferred version of the applicator 300 is shown in FIGS. 11–18.

The applicator 300 has a piston 310 that is shaped and sized to slidingly fit within an inner sleeve 320. The piston 310 has an external end 311 covered with a cap 312 and an internal end 313. The piston 310 may be hollow, as shown in the accompanying drawings, or solid.

The inner sleeve 320 has a flange 322 at a distal end 321 and a cap 324 at the opposing proximal end 323. The cap 324 has overlapping flaps 325 that cover the end 323. The overlapping flaps 325 will separate when pushed from within so that the device 10 will be able to pass through and between the flaps 325. The flaps 325 will thereafter return to their original position. It is preferred that the flaps 325 be formed so that they overlap in order to avoid the painful pinching that might be caused if the flaps met at their edges, as in known tampon applicators.

A channel 326 extends longitudinally within the inner sleeve 320. The device 10 (or 100 or 200) is folded so that it fits into a chamber 327 that is a section of the channel 326 between the cap 324 and the inner end 313 of the piston 310 when the piston 310 is placed inside the inner sleeve 320. As is best shown in FIG. 13, the piston 310 is not fully inserted into the inner sleeve 320 in order to provide room for the folded device 10.

An outer sleeve 330 is provided to cover the inner sleeve 320 with the exception of the flange 322. The outer sleeve 330 has a solid cap 332 at a first end 331 and contains a longitudinal channel 333 that is open at a second end 334 of the outer sleeve 330. The outer sleeve 330 is shaped to receive the inner sleeve 320 and is slightly larger so that the inner sleeve 320 fits within the channel 333 with an annular space 335 in between the inner sleeve 320 and the outer sleeve 330. A detent (not shown) may be provided on either the inner sleeve 320 or the outer sleeve 330 that will releasably engage a groove or pit (not shown) on the other of the inner sleeve 320 and the outer sleeve 330, in order to releasably secure the outer sleeve 330 on the inner sleeve 320. The space 335 is filled with a lubricant. The preferred lubricant is ASTROGLIDE water-soluble personal lubricant, available from BioFilm, Inc. of Vista, Calif. (The device 10 may also be coated with a lubricant before it is stored in the applicator 300.)

Figure 16:
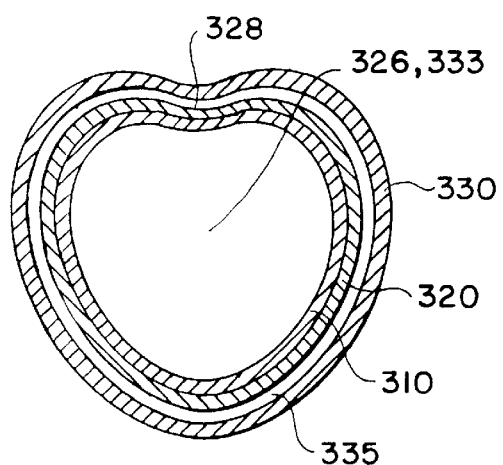
FIG. 16 is a cross-section of the applicator shown in FIG. 11, taken along plane 16–16'.
Figure 17:
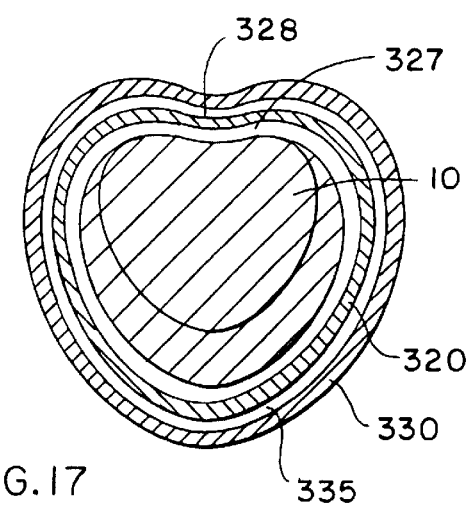
FIG. 17 is a cross-sectional view of the applicator shown in FIG. 11, taken along the plane 17–17'.

The piston 310, the inner sleeve 320, and the outer sleeve 330 have roughly heart-shaped cross-sections, as is seen best in FIGS. 16–17. It is preferred that at least the inner sleeve 320 have a roughly heart-shaped cross-section defining an external groove 328 so that the channel 326 will have a similar cross-section. The circumferentially asymmetric shape of the channel will serve to orient the device 10 within the chamber 327, with the cup 20 adjacent the groove 328. Preferably, both the piston 310, the inner sleeve 320, and the flange 322 will have a roughly heart-shaped cross-section to permit the user to orient the applicator by feel so that the device 10 will be released with the cup 20 adjacent the cervix and not the other way around.

It will be understood that other cross-sectional shapes may be employed in order to provide this orientation. Shapes with sharp angles, however, should be avoided when the component is to be used internally.

The combination of the applicator 300 and the device 10 loaded inside preferably is encased in an airtight and waterproof wrapping (not shown) during transportation and storage in order to maintain its sterility. The piston 310, the inner sleeve 320, and the outer sleeve 330 preferably are injection molded from any suitable thermoplastic and then assembled, together with the device 10, as shown in FIG. 12. The inner sleeve may be molded in a two-stage process in order to form the overlapping flaps 325.

Figure 18:
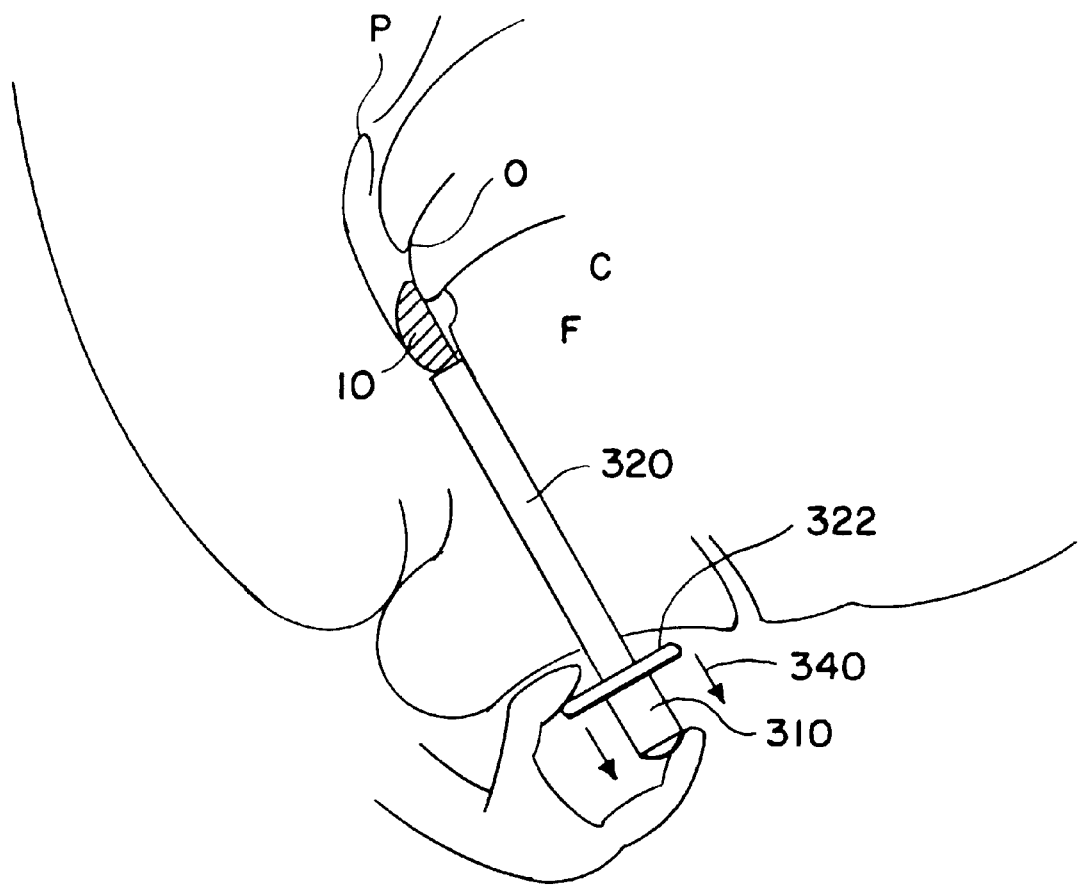
FIG. 18 is a side view of the applicator of FIGS. 11–17 shown releasing one of the devices of FIGS. 1–9 into the vagina of a female human being.

The device 10 is inserted as shown in FIG. 18. The user removes and discards the wrapping and then removes the external sleeve 330 from the inner sleeve 320. The external surface of the inner sleeve 320 will be covered with lubricant so that insertion is easier and more comfortable.

Using the fingers of one hand, the user introduces the cap 324 of the inner sleeve 320 into her vagina V and pushes the inner sleeve into the vagina V until the flange 322 is adjacent the entrance of the vagina V and the cap 324 is adjacent to the cervix. The inner sleeve 320 should be oriented by feel so that the groove 328 is on the upwards side of the inner sleeve 320. This will bring the side of the inner sleeve 320 having the groove 328 in contact with the anterior wall of the vagina. The user then will withdraw the inner sleeve 320 by pressing on the flange 322 (preferably with her thumbs) in the direction shown by the arrows 340 while maintaining the position of the piston 310 by pressure with a finger on the cap 312. The device 10 will be ejected through the flaps 325 from the end 32 of the inner sleeve 320 into the vagina V, in the correct orientation with respect to the cervix C, and trailing the retrieval string 70. Any lubricating gel attached to the device 10 will make it very slippery. The device 10 (or 100 or 200) will then "auto-seat" or automatically slip into position over the cervix, as shown in FIG. 12, after it unfurls and assumes its normal shape.

Accordingly, the reader will see that we have disclosed embodiments of a device for capturing and containing menstrual flow that are easy to use, safe, comfortable to wear, and permit sexual intercourse. We have also disclosed a method of making such a device and a method for using it.

Readers of skill in the art to which this invention pertains will understand that the foregoing description of the details of preferred embodiments is not to be construed in any manner as to limit the invention. Such readers will understand that other embodiments may be made which fall within the scope of the invention, which is defined by the following claims and their legal equivalents.

What is claimed is:

1. A device for capturing and containing menstrual flow from a female human being, comprising a cup made of flexible material shaped to sealingly contact the cervix between the anterior and posterior fornices, the cup containing an intravaginal reservoir for receiving menstrual flow and a port permitting menstrual flow discharged from the cervix to enter the reservoir.

2. The device according to claim 1 in which the port is covered by a membrane that permits the menstrual flow to enter the reservoir so that menstrual flow is captured and contained in the reservoir, whereby the captured menstrual flow is isolated from the cervix and the vaginal walls.

3. The device according to claim 1 further comprising a circumferentially extending rib at least partly affixed to the cup and shaped to extend into the anterior and posterior fornices in order to resiliently bias the cup against the cervix.

4. The device according to claim 3 in which the circumferentially extending rib projects away from and is detached from the cup at a posterior side of the cup in order to extend into the posterior fornix and thus bias the cup into position against the cervix.

5. The device according to claim 1 further comprising an absorbent material placed in the reservoir for absorbing the menstrual flow received in the reservoir.

6. The device according to claim 5 in which the port contains a fabric cover that permits the menstrual flow to enter the reservoir and retains the absorbent material in the reservoir, whereby the captured menstrual flow is isolated from the cervix and the vaginal walls.

7. The device according to claim 5 in which the absorbent material contains an antibacterial substance.

8. The device according to claim 1 further comprising at least one longitudinally extending rib affixed to the cup so that an anterior portion of the cup presses against the vaginal wall in order to bias the cup against the cervix.

9. A device for capturing and containing menstrual flow from a female human being, comprising:

(a) a cup made of flexible material and having a first side shaped to sealingly contact the cervix of the female human being between the anterior and posterior fornices and a port adjacent the os of the covered cervix;

(b) a pouch shaped wall attached to the cup opposite the first side and defining an intravaginal reservoir for receiving and containing menstrual flow from the port; and (c) means covering the port for permitting menstrual flow discharged from the cervix to enter but not leave the reservoir so that menstrual flow captured in the reservoir is contained in the reservoir and isolated from the cervix and the vaginal walls.

10. A method of capturing and containing the menstrual flow of a female human being, comprising the steps of:

placing in an end of an applicator a device for capturing and containing menstrual flow from a female human being, comprising a cup made of flexible material shaped to sealingly contact the cervix between the anterior and posterior fornices, the cup containing an intravaginal reservoir for receiving menstrual flow and a port permitting menstrual flow discharged from the cervix to enter the reservoir;

inserting the end of the applicator into the vagina;

releasing the device from the end of the applicator whereby the device automatically seats itself on the cervix; and withdrawing the applicator from the vagina.

11. The method according to claim 10 further comprising the step of applying lubricant to the device during or before the step of placing the device in the end of the applicator.

12. A method of making a device for capturing and containing the menstrual flow of a female human being, comprising the steps of:

molding a cup made of flexible material shaped to sealingly contact the cervix between the anterior and posterior fornices and having a port permitting menstrual flow discharged from the cervix to pass through the cup;

molding a pouch;

contacting the cup and the pouch so as to define an intravaginal reservoir for receiving and containing menstrual flow that enters the reservoir through the port; and fusing the pouch to the cup.

13. The method according to claim 12 further comprising the step of placing absorbent material between the cup and the pouch prior to the step of contacting the cup and the pouch so that the absorbent material will be contained in the reservoir.

14. An applicator and a device for collecting menstrual flow into the vagina of a female human being, comprising:

(a) a piston having an inner end and an outer end;

(b) a sleeve having a distal end and a proximal end and defining a channel between the distal end and the proximal end, the channel being shaped and sized so as to both receive the inner end of the piston so that the piston may move back and forth within the channel in sliding engagement and to store a device for collecting menstrual flow between the inner end of the piston and the proximal end of the sleeve; and (c) a flange attached adjacent the distal end of the sleeve, whereby the flange may be urged in a distal direction while maintaining the position of the piston with respect to the vagina in order to release the device into the vagina, wherein said device comprises a cup made of flexible material shaped to sealingly contact the cervix between the anterior and posterior fornices, the cup containing an intravaginal reservoir for receiving menstrual flow and a port permitting menstrual flow discharged from the cervix to enter the reservoir.

* * * * *